US009783699B2

United States Patent
Sanghi et al.

(10) Patent No.: US 9,783,699 B2
(45) Date of Patent: Oct. 10, 2017

(54) LAMINATES AND ARTICLES COMPRISING A BLOCK COPOLYMER COATING COMPRISING POLYORGANOSILOXANE AND POLYOLEFIN

(71) Applicant: 3M INNOVATIVE PROPERTIES COMPANY, St. Paul, MN (US)

(72) Inventors: Shilpi K. Sanghi, St. Paul, MN (US); Yu Yang, Eden Prairie, MN (US); Suresh S. Iyer, Woodbury, MN (US); Yongshang Lu, Woodbury, MN (US)

(73) Assignee: 3M INNOVATIVE PROPERTIES CO., St. Paul, MN (US)

( * ) Notice: Subject to any disclaimer, the term of this patent is extended or adjusted under 35 U.S.C. 154(b) by 189 days.

(21) Appl. No.: 14/426,168

(22) PCT Filed: Nov. 15, 2013

(86) PCT No.: PCT/US2013/070282
§ 371 (c)(1),
(2) Date: Mar. 5, 2015

(87) PCT Pub. No.: WO2014/081626
PCT Pub. Date: May 30, 2014

(65) Prior Publication Data
US 2015/0252215 A1 Sep. 10, 2015

Related U.S. Application Data

(60) Provisional application No. 61/728,511, filed on Nov. 20, 2012.

(51) Int. Cl.
*A61F 13/00* (2006.01)
*C09D 153/00* (2006.01)
(Continued)

(52) U.S. Cl.
CPC ........ *C09D 153/00* (2013.01); *A61F 13/0203* (2013.01); *A61F 13/0226* (2013.01);
(Continued)

(58) Field of Classification Search
None
See application file for complete search history.

(56) References Cited

U.S. PATENT DOCUMENTS 2,532,011 A  11/1950  Dahlquist
RE24,906 E  12/1960  Ulrich
(Continued)

FOREIGN PATENT DOCUMENTS

CH  505196  3/1971
EP  0254050  1/1988
(Continued)

OTHER PUBLICATIONS

McGrath, "Synthesis and Characterization of Segmented Siloxane Copolymers", American Chemical Society, Mar. 1998, vol. 39, No. 1, pp. 455-456.
(Continued)

*Primary Examiner* — Kim M Lewis
(74) *Attorney, Agent, or Firm* — Carolyn A. Fischer

(57) ABSTRACT

Intermediate laminates and articles comprising a low adhesion backsize coating are described. The laminate comprises a substrate having a major surface and opposing surface and a coating comprising a block copolymer disposed on a major surface of the substrate wherein the block copolymer comprises a polyorganosiloxane block and a polyolefin block, the polyolefin block having a melt point of at least 110° C. Also described are medical dressings comprising such laminate.

20 Claims, 1 Drawing Sheet

(51) Int. Cl.
*A61F 13/02* (2006.01)
*C09D 183/10* (2006.01)
*C09J 7/02* (2006.01)
*A61L 15/26* (2006.01)
*A61L 15/42* (2006.01)
*A61L 15/58* (2006.01)
*A61L 26/00* (2006.01)
*C08G 77/44* (2006.01)

(52) U.S. Cl.
CPC ............... *A61L 15/26* (2013.01); *A61L 15/42* (2013.01); *A61L 15/425* (2013.01); *A61L 15/58* (2013.01); *A61L 26/0014* (2013.01); *A61L 26/0085* (2013.01); *C09D 183/10* (2013.01); *C09J 7/0228* (2013.01); *A61L 2300/606* (2013.01); *C08G 77/44* (2013.01); *C09J 2201/122* (2013.01); *C09J 2201/606* (2013.01); *C09J 2423/005* (2013.01); *C09J 2423/105* (2013.01); *C09J 2451/005* (2013.01); *C09J 2453/005* (2013.01); *C09J 2475/006* (2013.01); *C09J 2483/005* (2013.01); *Y10T 428/1476* (2015.01); *Y10T 428/2848* (2015.01); *Y10T 428/31663* (2015.04)

(56) References Cited

U.S. PATENT DOCUMENTS

| | | | |
|---|---|---|---|
| 3,389,827 A | 6/1968 | Abere | |
| 3,445,389 A | 5/1969 | McKellar | |
| 3,573,334 A | 3/1971 | Wheeler, Jr. | |
| 3,645,835 A | 2/1972 | Hodgson | |
| 4,112,213 A | 9/1978 | Waldman | |
| 4,310,509 A | 1/1982 | Berglund | |
| 4,323,557 A | 4/1982 | Rosso | |
| 4,386,179 A | 5/1983 | Sterling | |
| 4,595,001 A | 6/1986 | Potter | |
| 4,737,410 A | 4/1988 | Kantner | |
| 5,088,483 A | 2/1992 | Heinecke | |
| 5,154,928 A * | 10/1992 | Andrews | A61F 13/0203 424/400 |
| 5,160,315 A | 11/1992 | Heinecke | |
| 5,214,119 A | 5/1993 | Leihr | |
| 5,229,179 A | 7/1993 | Kumar | |
| 5,346,951 A * | 9/1994 | Suwada | C08G 77/442 525/64 |
| 5,531,855 A | 7/1996 | Heinecke | |
| 5,622,711 A | 4/1997 | Chen | |
| 5,633,010 A | 5/1997 | Chen | |
| 5,641,835 A | 6/1997 | Smith | |
| 5,670,598 A | 9/1997 | Leir | |
| 5,744,541 A | 4/1998 | Sawaguchi | |
| 5,959,032 A | 9/1999 | Evans | |
| 6,264,976 B1 | 7/2001 | Heinecke | |
| 6,355,759 B1 | 3/2002 | Sherman | |
| 6,685,682 B1 * | 2/2004 | Heinecke | A61F 13/023 602/41 |
| 7,247,385 B1 | 7/2007 | Tzoganakis | |
| 7,943,120 B2 | 5/2011 | Toyoda | |
| 8,080,622 B2 | 12/2011 | Fujisawa | |
| 2002/0187326 A1 | 12/2002 | Kong | |
| 2008/0299347 A1 * | 12/2008 | Ukei | B29C 47/0021 428/41.8 |
| 2009/0318629 A1 | 12/2009 | Adoni | |
| 2010/0318052 A1 | 12/2010 | Ha | |
| 2011/0202029 A1 * | 8/2011 | Toro | A61F 13/15756 604/385.02 |
| 2014/0138025 A1 * | 5/2014 | Bartusiak | C09J 7/025 156/280 |
| 2015/0030796 A1 | 1/2015 | Boardman | |

FOREIGN PATENT DOCUMENTS

| | | |
|---|---|---|
| EP | 0507459 | 10/1992 |
| JP | S62-95337 | 5/1987 |
| JP | S63-101428 | 5/1988 |
| JP | H07-002915 | 1/1995 |
| JP | H07-258358 | 10/1995 |
| WO | WO 95-02642 | 1/1995 |
| WO | WO 96-30426 | 10/1996 |
| WO | WO 2009-073901 | 6/2009 |
| WO | WO 2012-103080 | 8/2012 |
| WO | WO 2014-081682 | 5/2014 |

OTHER PUBLICATIONS

Tanigawa, "Characterization of Thermo-Responsive Poly [N—(2-Hydroxypropyl) Methacrylamide-Dimethylsiloxane] Block Copolymers", Journal of the Society of Materials Science, Japan; Apr. 2006, vol. 55, No. 4, pp. 391-396.

International Search Report for PCT International Application No. PCT/US2013/070282, mailed on Feb. 11, 2014, 4 pgs.

* cited by examiner

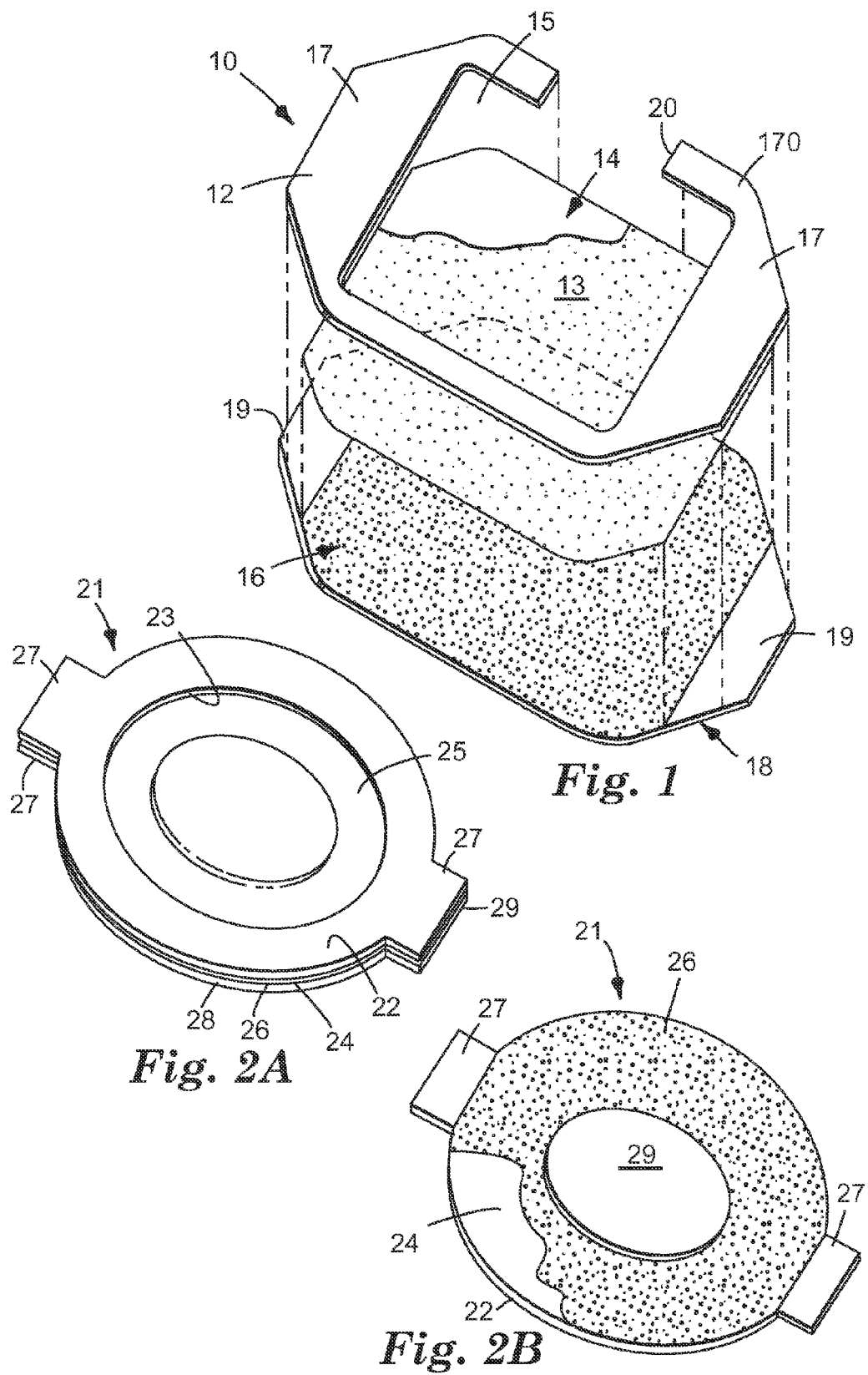

LAMINATES AND ARTICLES COMPRISING A BLOCK COPOLYMER COATING COMPRISING POLYORGANOSILOXANE AND POLYOLEFIN

CROSS REFERENCE TO RELATED APPLICATIONS

This application is a national stage filing under 35 U.S.C. 371 of PCT/US2013/070282, filed Nov. 15, 2013, which claims priority to U.S. Provisional Application No. 61/728,511, filed Nov. 20, 2012, the disclosure of which is incorporated by reference in their entirety herein.

FIELD

The invention relates to (e.g. intermediate) laminates and articles comprising a (e.g. low adhesion backsize) coating comprising a block copolymer having a polyorganosiloxane block and polyolefin block.

SUMMARY

In one embodiment, a laminate is described comprising a substrate having a major surface and opposing surface; and a coating comprising a block copolymer disposed on a major surface of the substrate wherein the block copolymer comprises a polyorganosiloxane block and a polyolefin block, the polyolefin block having a melt point of at least 110° C.

Also described are medical dressings comprising the laminate described herein.

BRIEF DESCRIPTION OF THE DRAWINGS

The invention may be further illustrated by reference to the accompanying drawings wherein:

FIG. 1 is a top perspective view of one embodiment of a medical dressing;

FIG. 2A is a top perspective view of another embodiment of a medical dressing; and FIG. 2B is a bottom perspective view of the dressing of FIG. 2A with the liner removed.

DETAILED DESCRIPTION

Presently described are block copolymers suitable for use as a low adhesion backsize ("LAB") coating. The block copolymers comprise at least one polyorganosiloxane block and at least one polyolefin block. The polyolefin block is semi-crystalline having a melt point of at least 110° C. The block copolymer typically has the structure:

$$A[\text{-}L\text{-}B]_n$$

wherein A is a polyorganosiloxane block and B is a polyolefin block. L is a covalent bond or a divalent linking group. In some favored embodiments, L is the reaction product of an amine or hydroxyl and an anhydride.

In some embodiments, n is 1, and the block copolymer can be characterized as having a linear diblock (A-B) structure. In other embodiments, n is 2 and the block copolymer can be characterized as having a linear triblock (B-A-B) structure wherein B are polyolefin endblocks and A is the polyorganosiloxane midblock. In yet other embodiments, n is 3 or greater, and the block copolymer may be characterized as a grafted block copolymer. The grafted block copolymer typically comprises a polyorganosiloxane backbone A and polyolefin side chains. The grafted copolymer may optionally further comprise polyolefin end block(s).

The polyolefin block preferably comprises a semi-crystalline polyolefin homopolymer or copolymer having a melt point of at least 110° C., 115° C., or 120° C. Polyethylene and especially polypropylene polymers are preferred in few of their relatively high melting point as a result of having a relatively high level of crystallinity. The melting of polypropylene occurs over a range. Thus, the melting point is determined by finding the highest temperature as measured according to differential scanning calorimetry.

Medium- and high-density polyethylene has a melting point in the range 120 to 130° C. (248 to 266° F.). In some embodiments, the polyolefin block has a melting point of at least 120° C., as can be provided from syndiotactic polypropylene (having a crystallinity of 30%) and a melting point of 130° C. Polypropylene that is predominantly isotactic typically has a melting point that ranges from 160 to 166° C. (320 to 331° F.). In some embodiments, the polyolefin block has a melting point of at least 130° C., 135° C., 140° C., 145° C., 150° C., 155° C. or 160° C. Polypropylene having such melting point may comprise a combination of syndiotactic and isotactic repeat units. In yet other embodiments, the polyolefin block has a melting point of at least 165° C. or 170° C., as can be provided by 100% isotactic polypropylene having a melting point of 171° C. (340° F.).

In yet other embodiments, the polyolefin block is a copolymer of polyethylene and polypropylene copolymer. For example, a random copolymer of polyethylene and predominantly isotactic polypropylene has a melting point between the melting point of a polyethylene homopolymer and isotactic polypropylene. In some embodiments, the polyolefin copolymer comprises repeat units derived from ethylene and/or propylene and one or more other saturated or unsaturated $C_4$-$C_{12}$ olefin comonomers. When the comonomer is saturated, the crystalline polyolefin block may be characterized as a polyalkylene copolymer. When the comonomer is unsaturated, the polymer may be characterized as a polyalkene copolymer.

Unless specified otherwise, throughout the application "molecular weight" refers to the number average molecular weight. The molecular weight of the polyorganosiloxane block is typically at least 500 g/mole, 600 g/mole, 700 g/mole, or 800 g/mole. The molecular weight of the polyorganosiloxane block is typically no greater than 150,000 g/mole or 100,000 g/mole. In some embodiments, the molecular weight of the polyorganosiloxane block is at least 900 g/mole or 1000 g/mole and may range up to 5,000 g/mole. In other embodiments, the molecular weight of the polyorganosiloxane block is at least 2000 g/mole or 3000 g/mole or 4000 g/mole or 5000 g/mole and may range up to 25,000 g/mole. In yet other embodiments, the molecular weight (Mn) of the polyorganosiloxane block is at least 10,000 g/mole or 15,000 g/mole or 20,000 g/mole or 25,000 g/mole.

The molecular weight of the (e.g. polypropylene) polyolefin block is also typically at least 500 g/mole, 600 g/mole, 700 g/mole, or 800 g/mole. In some embodiments, the molecular weight of the (e.g. polypropylene) polyolefin block is at least 1500 or 2000 g/mole. In some embodiments, the molecular weight of the (e.g. polypropylene) polyolefin block is at least 3000, 4000, or 5000 g/mole. In some embodiments, the molecular weight of the (e.g. polypropylene) polyolefin block is no greater than 50,000 g/mole, 40,000 g/mole, 30,000 g/mole or 20,000 g/mole. When the polyolefin block is a polypropylene homopolymer the number of repeats is about 24 to obtain a molecular weight of about 1,000 g/mole. However, when the polyolefin block is a polypropylene copolymer and the comonomer has greater than 3 carbon atoms, the number of repeat units may be lower. The polyolefin block is generally a homopolymer or copolymer comprising at least 5, 6, 7, 8, 9, or 10 total repeat units.

The molecular weight of the block copolymer is generally equal to the sum of the molecular weight of the blocks. Generally the polyorganosiloxane and polyolefin materials are selected such that the block copolymer has a molecular weight of at least 1,000 g/mole; 1,500 g/mole; or 2,000 g/mole and no greater than 250,000 g/mole. In some embodiments, the molecular weight of the block copolymer is no greater than 200,000 g/mole, 150,000 g/mole, or 100,000 g/mole.

When the block copolymer is a diblock (and both blocks have the same molecular weight), the block copolymer typically comprises about 50 wt.-% polyorganosiloxane. In some embodiments, the block copolymer comprises less than 50 wt.-% polyorganosiloxane. For example, when the block copolymer is a triblock (and both blocks have the same molecular weight), the block copolymer typically comprises about 33 wt.-% polyorganosiloxane. In yet another embodiment, a graft copolymer may comprise a polyorganosiloxane backbone and polyolefin graft(s) wherein the polyolefin graft(s) have a molecular weight 2, 3, 4, 5, or 6 times that of the polyorganosiloxane. The minimum amount of polyorganosiloxane is typically at least 15 wt-% of the total weight of the block copolymer. Block copolymer having at least 45 or 50 or 55 wt-% polyolefin are favorable for heat sealing. High concentrations of polyolefin can also be amenable to reducing cost of the block copolymer.

In other embodiments, the block copolymer comprises greater than 50 wt.-% polyorganosiloxane. This can be achieved when the polyorganosiloxane block has a significantly higher molecular weight than the polyolefin block. The maximum amount of polyorganosiloxane is typically at least 75 wt-% of the total weight of the block copolymer. Block copolymers having higher concentrations of polyorganosiloxane can provide better release properties.

In some embodiments, the block copolymers can be prepared by reacting an amine- or hydroxyl-functional polyorganosiloxane with an anhydride-functional polyolefin block. In other words the polyorganosiloxane block and polyolefin block are linked by the reaction product of an amine or hydroxyl group with an anhydride.

The amine-functional polyorganosiloxane can be prepared by a variety of methods. Methods of synthesizing such materials is described in U.S. Pat. No. 5,214,119 and U.S. Pat. No. 6,355,759.

Various amine-functional polyorganosiloxane materials are commercially from Gelest Inc., Morrisville Pa.; Wacker Chemie AG, Munich Germany; and Genesse Polymer Corporation, Burton, Mich. Hydroxy-functional polyorganosiloxane (e.g. diol) materials are also commercially available from Gelest Inc.

The amine groups of the amine-functional polyorganosiloxane are primary, secondary, or a combination thereof.

Anhydride-functional polyolefins can be prepared by a free radical reaction of maleic anhydride with polyolefin.

Anhydride-functional polypropylene polymers are commercially available from Baker Hughes, Polymer Division, Send Springs, Oklahoma under the trade designations "PP-X-10081", "PP-X-10082", "PP-X-10065", and "PP-X-10053".

The anhydride functional group of the polyolefin is typically a succinic anhydride or a derivative thereof.

Succinic anhydride-functional polyolefins can be represented by the formula:

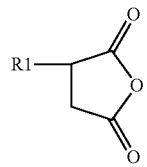

wherein R' is a polyolefin polymer having a melt point of at least 110° C.

For embodiments wherein the block copolymer is a diblock copolymer comprising a single polyorganosiloxane block and a single (e.g. polypropylene) polyolefin block, a monofunctional (e.g. amine or hydroxyl) polyorganosiloxane can be reacted with a mono-anhydride (e.g. polypropylene) polyolefin. The diblock copolymer can be represented by the following formula:

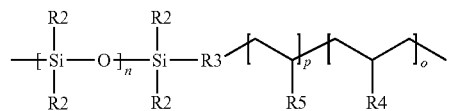

wherein R2 is hydrogen, C1-C6 alkyl or nitrile;

n is the number of siloxane repeat unit,

R3 is the reaction product of an amine or hydroxyl functional group and an anhydride functional group;

p is the number of polyethylene and/or polypropylene repeat units;

for each m, R5 is independently hydrogen (i.e. ethylene repeat unit) or methyl (i.e. propylene repeat unit) R4 is a C1-C8 alkylene or alkene; and o is the number of saturated alkylene of unsaturated alkene repeat units independently having 4 to 12 carbon atoms.

R2 is most typically methyl. The number of siloxane repeat units, n, is greater than 1 and is a value such that the polyorganosiloxane block has the molecular weight ranges previously described. The number of polyethylene and/or polypropylene repeat units, p, is typically at least 5, 6, 7, 8, 9, or 10 as previously described. In some embodiments, o is zero and the polyolefin block is a polypropylene or polyethylene homopolymer. In other embodiments, n is at least 1, or greater than 1, such as 2, 3, 4, or 5. The number of comonomer repeat units is typically less than or equal to the number of polyethylene and polypropylene repeat units. In some embodiments, the divalent linking group, R3, independently has one of the following structures:

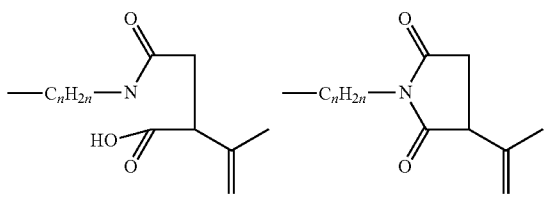

-continued

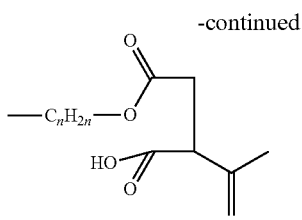

A diblock copolymer can also be prepared by hydrosilylation reaction of a double bond terminated polyolefin with a polyorganosiloxane polymer having a terminal hydride. The diblock copolymer can be represented by the following formula:

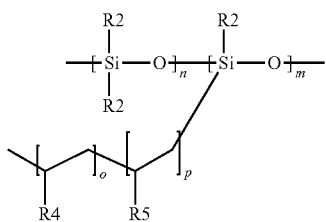

wherein R2, R4, R5, n, o, and p are the same as previously described and m is the number of siloxane groups having a polyolefin graft.

For embodiments wherein the block copolymer is a linear triblock copolymer comprising a polyorganosiloxane midblock and (e.g. polypropylene) polyolefin endblocks, a polyorganosiloxane diamine or diol can be reacted with a monoanhydride (e.g. polypropylene) polyolefin. The triblock copolymer can be represented by the following formula:

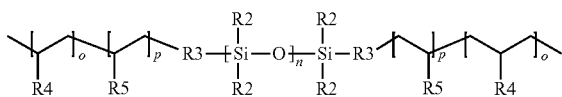

wherein R2, R3, R4, R5, n, o, and p are the same as previously described.

For embodiments wherein the block copolymer is a graft copolymer comprising a polyorganosiloxane backbone and (e.g. polypropylene) polyolefin side chain, a polyorganosiloxane comprising one or more pendant amines or hydroxyls can be reacted with a mono-anhydride (e.g. polypropylene) polyolefin. The grafted copolymer can be represented by the following formula:

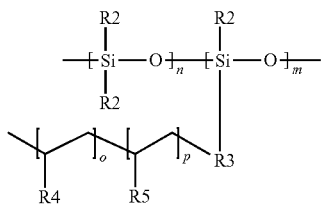

wherein R2, R3, R4, R5, n, o, and p are the same as previously described and m is the number of siloxane groups having a polyolefin graft.

Regardless of the reaction scheme, the reactions are conducted in a dry (i.e. non-aqueous) solvent, or mixtures of solvents, protected from atmospheric moisture. The solvents are unreactive with the functional groups of the starting materials. The starting materials and final products typically remain completely miscible in the solvents during and after completion of the polymerization. Suitable solvents include polar liquids, such as alcohols, ethers, esters, and chlorinated hydrocarbons, with tetrahydrofuran and methylene chloride being especially useful. Solvents are determined by the nature of the reagents. Secondary alcohols, such as isopropanol or 2-butanol, are typically utilized, either alone, or in combination with non-polar solvents such as toluene or cyclohexane.

The block copolymer composition may optionally comprise suitable additives such as pigments, dyes, and fillers. Particularly when the block copolymer composition is utilized on an industrial tape or label article, light stabilizing compound are commonly added.

The polyorganosiloxane block copolymer compositions described herein, depending upon their viscosity, can be coated via any of a variety of conventional coating methods, such as roll, knife, or curtain coating, or (e.g. hot melt) extrusion coating. When the block copolymer composition is applied as a solvent-based coating, the coating is dried after application.

The (solvent-less) coated block copolymer composition typically has a thickness of at least 50 nm or 100 nm (0.1 microns) and no greater than 20 mils. In some embodiments, the thickness is at least 0.5, 1 or 2 microns and no greater than 50, 40, 30, 20, or 10 microns.

The block copolymers of the present invention are suitable for use as low adhesion backsize (LAB) coatings. In some embodiments, the low adhesion backsize (LAB) coating comprises the described block copolymer in the absence of adhesion adjusting components such as tackifiers, plasticizers, and waxes. In other embodiments, the bock copolymer compositions comprises up to 5, 10 or 15 wt-% of such adhesion adjusting components.

Low adhesion backsize coating are typically applied to an exposed surface of a planar surface such as a nonwoven or polymeric film substrate. In some embodiments, the low adhesion backsize coating improves the slip or in other words reduces the friction as compared to the backing substrate in the absence of such coating. In some embodiments, the coefficient of friction is reduced by 20%, 30%, 40%, 50%, 60%, 70% or 80% as compared to the substrate in the absence of such coating. The coefficient of friction can be less than 0.4, or 0.35, or 0.3, or 0.25, or 0.20. In some embodiments, the coefficient of friction is at least 0.02 or 0.05 or 0.10.

In some embodiments, low adhesion backsize (LAB) coating is utilized on an (e.g. intermediate) laminate or article that further comprise a pressure sensitive adhesive, such as tapes, labels and other types of PSA-coated sheets. Some embodiments of such articles utilizing a polyvinyl carbamate LAB coating are described in U.S. Pat. No. 2,532,011; incorporated herein by reference. The LAB-coated surface provides a surface to which the adhesive does not permanently adhere, so that the adhesive releases therefrom prior to use.

A backing substrate having a LAB is particularly useful for providing an adhesive article such as a tape in roll form. In this case, adhesive is coated onto the side of the backing substrate opposite the LAB so that when the adhesive coated backing substrate is rolled, the adhesive contacts the LAB. The adhesive adheres well enough to the LAB so that the roll does not come undone or "telescope", yet not so well that the tape cannot be unrolled.

The block copolymers of this invention may be prepared to give varying amounts of release through variations in the molecular weight (Mn) of the polyorganosiloxane and polyolefin blocks as well as the number of each block of the block copolymer structure. In general, the amount of release can vary from 1.0N/dm or less to about 35N/dm. LABs for tapes in roll form typically exhibit release values in the range of from about 6 to about 35N/dm.

As the concentration of polyorganosiloxane increases the release values can decrease. For premium release coatings (i.e., release coatings having release values of less than about 2N/dm), a higher content of polyorganosiloxane is required in the formulation, e.g. from about 25 to 50 percent by weight polyorganosiloxane. In applications where moderate release values are acceptable, the polysiloxane content may be reduced to lower levels, for example, 15% by weight and lower.

Regardless of whether the composition is intended to reduce the coefficient of friction of the substrate to which it is applied and/or release from a pressure sensitive adhesive, the block copolymer compositions can be applied to at least a portion of at least one major surface of a suitable flexible or inflexible backing substrate material and dried to produce low adhesion sheet materials. Useful flexible backing substrate materials include paper, plastic films such as poly(propylene), poly(ethylene), poly(vinyl chloride), poly(tetrafluoroethylene), polyurethane, polyester [e.g., poly(ethylene terephthalate)], polyimide film, cellulose acetate, and ethyl cellulose. Backing substrates can also be of woven fabric formed of threads of synthetic or natural materials such as cotton, nylon, rayon, glass, or ceramic material, or they can be of nonwoven fabric such as air-laid webs of natural or synthetic fibers or blends of these. In addition, suitable backing substrates can be formed of metal, metallized polymeric film, or ceramic sheet material.

The backing substrate may optionally comprise a primer or tie layer disposed between the substrate and low adhesion coating comprising the block copolymer described herein.

The thickness of the backing substrate is typically no greater than 200, or 100, or 50, or 25 μm. The thickness is typically at least 15 μm.

The coated sheet materials can take the form of any article conventionally known to be utilized with PSA compositions, such as labels, tapes, transfer tapes (comprising a film of the PSA borne on at least one release liner), signs, marking indices, as well as medical or wound dressings.

In one embodiment, the block copolymers are useful as a low adhesion backsize coating of a medical or wound dressing.

Wound dressings often comprise a conformable backing substrate to which the LAB is coated. The backing substrate is selected to provide a sufficiently impermeable barrier to the passage of liquids and at least some gases. Representative backing substrates may include non-woven and woven fibrous webs, knits, films, foams polymeric films and other familiar backing substrate materials. The preferred backing substrate materials include thin elastomeric backing substrates. These types of backing substrates help ensure conformability and high adhesion around the wound site. Preferred backing substrate materials may be translucent or transparent polymeric films including polyurethanes (e.g. ESTANE®, TEXIN®), polyether polyesters (e.g. HHTREL), polyether amides (e.g. PEGAX) as well as polyolefins (e.g. ENGAGE).

Suitable backing substrate materials also include nonwoven fibrous webs, woven fibrous webs, knits, films and other familiar backing substrate materials. The backing substrate materials are typically translucent or transparent polymeric elastic films. The backing substrate can be a high moisture vapor permeable film backing substrate U.S. Pat. No. 3,645,835 describes methods of making such films and methods for testing their permeability.

The backing substrate typically has an upright moisture vapor transmission rate of at least 1000, or 1500, or 2000, or 2500, or 3000 g/m$^2$/24 hrs. The inverted moisture vapor transmission rate of the backing substrate is typically at least 10,000, or 15,000, or 20,000 g/m$^2$/24 hrs. The low adhesion backside coating is applied at a thickness such that the presence of the LAB coating does not substantially decrease the MVTR of the backing substrate.

The wound dressing typically transmits moisture vapor at a rate equal to or greater than human skin. In some embodiments, the adhesive coated backing transmits moisture vapor at a rate of at least 200 or 250 g/m$^2$/24 hrs/37° C./100-10% RH, frequently at least 700 g/m$^2$/24 hrs/37° C./100-10% RH, when the adhesive is in contact with water vapor and not water (i.e. upright MVTR) and most typically at least 2000 g/m$^2$/24 hrs/37° C./100-10% RH when adhesive is in contact with water, using the inverted cup method (such as described in U.S. Pat. No. 4,595,001).

For embodiments wherein fluids are actively removed from a sealed environment provided by the wound dressing (such as described in US 2010/0318052) a relatively high moisture vapor permeable backing substrate may not be required. As a result, some other potentially useful backing substrate materials may include, e.g., metallocene polyolefins and SBS and SIS block copolymer (e.g., KRATON type) materials could be used.

The backing substrates may also preferably be conformable to anatomical surfaces. As such, when the backing substrate is applied to an anatomical surface, it conforms to the surface even when the surface is moved. The backing substrate may also be conformable to animal anatomical joints. When the joint is flexed and then returned to its unflexed position, the backing substrate may stretch to accommodate the flexion of the joint, but is resilient enough to continue to conform to the joint when the joint is returned to its unflexed condition. A description of this characteristic of backing substrates can be found in issued U.S. Pat. Nos. 5,088,483 and 5,160,315. Examples of some potentially suitable backing substrates may include elastomeric polyurethane, polyester, or polyether block amide films. These films combine the desirable properties of resiliency, high moisture vapor permeability, and transparency.

Commercially available examples of backing substrate materials may include the thin polymeric films sold under the tradenames TEGADERM (3M Company), BIOSITE (Johnson & Johnson Company), OPSITE (Smith & Nephew), etc. Many other backing substrates may also be used, including those commonly used in the manufacture of surgical incise drapes (e.g., incise drapes manufactured by 3M Company under the tradenames STERIDRAPE and IOBAN), etc.

Pressure sensitive adhesives for wound dressings include those based on acrylates, polyurethanes, KRATON and other block copolymers, silicones, rubber based adhesives (including natural rubber, polyisoprene, polyisobutylene, butyl rubber etc.) as well as combinations of these adhesives. The adhesive component may contain tackifiers, plasticizers, rheology modifiers as well as active components including for example an antimicrobial agent. In some embodiments, the pressure sensitive adhesive has a relatively high moisture vapor transmission rate to allow for moisture evaporation, as previously described with regard to the backing substrate. This can be achieved by pattern coating, etc. as known in the art.

Specific adhesives that are commonly applied to the skin include acrylate copolymers such as described in U.S. Pat. No. RE 24,906, particularly a 97:3 isooctyl acrylate:acrylamide copolymer. Another example may include a 70:15:15 isooctyl acrylate:ethyleneoxide acrylate acrylic acid terpolymer, as described in U.S. Pat. No. 4,737,410 (Example 31). Other potentially useful adhesives are described in U.S. Pat. Nos. 3,389,827; 4,112,213; 4,310,509; and 4,323,557. Inclusion of medicaments or antimicrobial agents in the adhesive is also contemplated, as described in U.S. Pat. Nos. 4,310,509 and 4,323,557.

Release liners typically protect the pressure sensitive adhesive used to attach the dressings to the patient and in some embodiments create a sealed cavity. Release liners that may be suitable for use in the medical dressing can be made of supercalendered kraft paper, glassine paper, polyethylene, polypropylene, polyester or composites of any of these materials. The liners are coated with release agents such as fluorochemicals or silicones such as described in US 20120/0318052.

An absorbent material may also be used in conjunction with the medical dressings described herein. The absorbent materials can be manufactured of any of a variety of materials including, but not limited to, woven or nonwoven materials such as cotton or rayon. Absorbent pad is useful for containing a number of substances, optionally including antimicrobial agents, drugs for transdermal drug delivery, chemical indicators to monitor hormones or other substances in a patient, etc.

The absorbent may include a hydrocolloid composition, including the hydrocolloid compositions described in U.S. Pat. Nos. 5,622,711 and 5,633,010, the disclosures of which are hereby incorporated by reference. The hydrocolloid absorbent may comprise, for example, a natural hydrocolloid, such as pectin, gelatin, or carboxymethylcellulose (CMC) (Aqualon Corp., Wilmington, Del.), a semi-synthetic hydrocolloid, such as cross-linked carboxymethylcellulose (X4ink CMC) (e.g. Ac-Di-Sol; FMC Corp., Philadelphia, Pa.), a synthetic hydrocolloid, such as cross-linked polyacrylic acid (PAA) (e.g., CARBOPOL™ No. 974P; B.F. Goodrich, Brecksville, Ohio), or a combination thereof.

Absorbent materials may also be chosen from other synthetic and natural hydrophilic materials including polymer gels and foams. The foams can be open cell polyurethane, closed cell polyurethane.

The medical dressings can further comprise valves, barrier elements, septum elements, at least one of a number of active ingredients etc. as described in US 2010/0318052; incorporated herein by reference.

In some instances, the backing substrates used in the medical dressings may be so flexible and supple such that when a release liner is removed from the backing substrate, the backing substrate may tend to fold and adhere to itself, interfering with the smooth, aseptic application of the dressing to a patient's skin.

Carrier materials such as frames, handles, stiffening strips, etc. as known in the art are one way to prevent the backing substrate from folding and adhering to itself. Carrier materials can include, but are not limited to, ethylene vinyl acetate copolymer or ethylene acrylic acid coated papers and polyester films.

The carrier material can be heat seal-bonded to the backing substrate. In such embodiments, the low adhesion coating described herein is compatible with the heat seal bond between the carrier and the backing substrate and also retains its low coefficient of friction characteristics after heat sealing. Further the low adhesion coating can also reduce the heat seal bond strength between the backing and the carrier such that the carrier is retained, yet can be easily removed during use.

One illustrative method of manufacture is described in U.S. Pat. No. 5,531,855. The method comprises die cutting windows into a carrier material. The windows typically lie in the center of the carrier web. The die cutting is commonly accomplished using rotary die cutting equipment. After the windows have been die cut in the carrier material, they are optionally removed. Removal of the windows defines the inner edge of the frame of carrier material which is located around the perimeter of each of the dressings. The windows die cut into the carrier material can be removed using a number of methods known to those skilled in the art. Those methods could include the use of vacuum, air pressure, gravity, and nip rolls having a small diameter which cause the windows to be removed from the framed carrier material.

The carrier material forming the window (which is removed) is typically not heat sealed to the backing substrate as is the remainder of the carrier material making up the frame of each dressing.

After the low adhesion coating step and the die cutting and window removal steps are completed, the carrier material (with windows removed) is heat sealed to the top face of the backing substrate, over the low adhesion coating.

Additional control over the heat sealing process can be accomplished a number of ways. It can include cavities in the heated rolls used in heat sealing or other means, such as texturing the nip rolls which compress the adhesive composite web against the heated roll during processing.

One illustrative medical dressing is depicted in FIG. 1 and described in U.S. Pat. No. 5,531,855; incorporated herein by reference. The adhesive composite dressing 10 comprises a (e.g. conformable) backing substrate 14; a low adhesion coating comprising a polyorganosiloxane block copolymer as described herein 13 on a top face of the backing substrate 14; a carrier 170 attached to the top face of the backing substrate 14 over the low adhesion coating 13; a pressure-sensitive adhesive 16 on a bottom face of the backing substrate 14; and a liner 18 attached to the exposed surface of pressure-sensitive adhesive 16.

The carrier 170 is typically attached to backing substrate 14 through low adhesion coating 13 with a heat seal bond. In one embodiment, a (e.g. rectangular) window portion cut in the carrier 170 is removed creating a frame 12 and a window 15 exposing a portion of the top face of the backing substrate 14. Carrier (e.g. frame) 12 provides rigidity to the backing substrate 14 after liner 18 is removed. However, the removal of the window portion of the carrier material 170 is optional. In either embodiment, the low adhesion coating 13 becomes incorporated into and does not impair the formation of a heat seal bond between the carrier (e.g. frame) 12 and backing substrate 14. Further, the heat seal bond comprises materials from all three layers—i.e. the carrier material, the low adhesion coating and the backing substrate.

Liner 18 and carrier (e.g. frame) 12 can both include tabs 17 and 19 that extend beyond the perimeter of backing substrate 14 to provide a means of applying the dressing without contacting the adhesive 16.

The heat seal bond between the carrier 170 and the backing substrate 14 is stronger than the bond between the adhesive 16 and the liner 18. That difference ensures that the backing substrate 14 remains attached to the frame 12 when liner 18 is removed from the adhesive composite dressing 10.

The dressing 10, having frame 12 that includes opening 20 such that the frame 12 does not extend completely around the perimeter of the backing substrate 14 can be placed over catheters or other devices while still attached to the frame 12 to increase the ease of handling of backing substrate 14.

In use, liner 18 is first removed from the adhesive composite dressing 10 leaving the frame 12/backing substrate 14/pressure-sensitive adhesive 16 intact. The user can then manipulate the adhesive composite dressing 10 using tabs 17 on the frame 12 while viewing the area to which the dressing 10 will be attached through window 15, as the (e.g. transparent or translucent) backing substrate 14.

The low adhesion coating 13 on the backing substrate 14 can also reduce dressing changes due to unwanted dressing removal when other tapes or devices are placed on the dressing 10 and removed. The low adhesion coating 13 can also reduce the surface friction of the dressing 10 on linen or other fabrics, thereby offering additional protection against the accidental removal of dressings 10. The low adhesion coating 13 reduces the friction of dressing 14 against cotton and thereby protects the skin from damage against friction and reduces pressure ulcer occurrence. Further, the low adhesive coating on the backing substrate 14, heat sealed to carrier 170, does not necessitate the removal of the carrier material from window 15 prior to use by the end user.

FIGS. 2A and 2B, depict an alternate embodiment of a medical dressing 21. As shown, the medical dressing 21 is an adhesive composite comprising a frame 22, a backing substrate 24, adhesive 26 and a liner 28. The backing substrate comprises the block copolymer coating described herein on the surface between the backing and the frame. Liner 28 may have opposing tabs 29 for handling, and frame 22 also includes tabs 27 for handling.

Medical dressing 21 also includes an open area or window 25 in frame 22 which exposes a portion of the top surface of backing 24. Frame 22 extends around the entire perimeter of backing 24 and includes a control depth die cut 23 to facilitate removal of frame 22 from backing 24 after the dressing 21 has been applied to a patient.

FIG. 2B is a bottom view of medical dressing 1 with liner 28 removed to expose the adhesive layer 26 and absorbent pad 29 disposed proximate the center of the dressing 21. Absorbent pad 29 can be manufactured of a number of materials including, but not limited to, woven or nonwoven cotton or rayon. Absorbent pad 29 is useful for containing a number of substances, including antimicrobial agents, drugs for transdermal drug delivery, chemical indicators to monitor hormones or other substances in a patient, etc. Furthermore, although absorbent pad 29 is shown as centered on dressing 21, it can take any appropriate shape and/or can be located off-center on the dressing 21 as desired.

Removal of the frame material 22 from the window area 25 of dressing 21 can be advantageous. Pad 29 tends to deform the backing 24 and cause delamination between the frame material 22 in window 25 if that material is still present when pad 29 is placed on dressing 21.

This invention is further illustrated by the following examples which are not intended to be limiting in scope. Unless indicated otherwise, the molecular weights refer to number average molecular weights. All parts, percentages and ratios are by weight unless otherwise specified.

EXAMPLES

Objects and advantages of this invention are further illustrated by the following examples, but the particular materials and amounts thereof recited in these examples, as well as other conditions and details, should not be construed to unduly limit this invention. These examples are merely for illustrative purposes only and are not meant to be limiting on the scope of the appended claims.

Materials

Unless otherwise noted, all parts, percentages, ratios, etc., in the examples and in the remainder of the specification are by weight. Unless otherwise noted, all chemicals were obtained or are available from, chemical suppliers such as Aldrich Chemical Company, Milwaukee, Wis.

| Designation | Description | Supplier |
|---|---|---|
| HMS-064 | Methylhydrosiloxane-dimethylsiloxane copolymer $M_n$ = 55K-65K | Gelest Inc., Morrisville, PA |
| PP-X-10081 | Polypropylene terminated with double bond Mn = 8000 | Baker Hughes, Polymer Division, Send Springs, OK |
| PP-X-10065 | Polypropylene terminated with anhydride, Mn = 1178 | Baker Hughes, Polymer Division, Send Springs, OK |
| PP-X-10082 | Polypropylene terminated with anhydride, Mn = 6418 | Baker Hughes, Polymer Division, Send Springs, OK |
| PP-X-10053 | PP copolymerized with 1-hexalene and terminated with anhydride, Mn = 2654 | Baker Hughes, Polymer Division, Send Springs, OK |
| WACKER FLUID NH 130D | Polydimethylsiloxane diamine, Mw = 11496 | Wacker Chemie AG, Münich, Germany |
| DMS-C21 | Polydimethylsiloxane diol, Mn 1178 | Gelest Inc., Morrisville, PA |
| GP-4 | Polydimethylsiloxane multi-amine, equivalent Mn = 1182.03 | Genesee Polymers Corporation, Burton, MI |
| MCR-A11 | Monoaminopropyl terminated polydimethylsiloxane Mn = 900 | Gelest Inc., Morrisville, PA |
| SIP 6831.2 | Platinum-divinyl tetramethyl disiloxane complexes in xylene | Gelest Inc., Morrisville, PA |
| ESTANE 58237 | Ether based polyurethane film, 0.9-1.1. mil (22.9 micrometers-27.9 micrometers) thick | Lubrizol Corporation, Cleveland, OH |

Test Methods

Method for Determining Static and Kinetic Coefficient of Friction

The static and kinetic coefficients of friction (S-COF and K-COF, respectively) of the coated films (prepared in examples described below) were tested against 100% cotton sheets according to the ASTM D1894 08 (Standard test method for static and kinetic coefficients of friction of plastic film and sheeting, Rev. 11 (2011), obtained from HIS Inc., Englewood, Colo.) except that the test specimen was attached to the sled and cotton sheet was attached to the plane.

Method for Determining Heat Sealing Compatibility

A carrier was heat sealed to the coated backing substrate using a pressure of 50 psi. The carrier was a (78#) paper substrate having a silicone release side and a polyethylene coated side. The polyethylene side of the carrier was contacted with the dried block copolymer LAB coating of the backing substrate when heat sealed. The dwell time (in seconds) and heat seal temperature were recorded and are reported in the table below.

Method for Determining Moisture Vapor Transmission Rate (MVTR)

Upright MVTR

The upright MVTR was measured according to ASTM E96-80 using a modified Payne cup method. A 3.8 cm diameter sample was placed between adhesive-containing surfaces of two foil adhesive rings, each having a 5.1 cm$^2$ elliptical opening. The holes of each ring were carefully aligned. Finger pressure was used to form a foil/sample/foil assembly that was flat, wrinkle free, and had no void areas in the exposed sample.

A 120 mL glass jar was filled with approximately 50 g of tap water that contained a couple drops of 0.02% (w/w) aqueous Methylene Blue USP (Basic Blue 9, C.I.52015) solution, unless specifically stated in an example. The jar was fitted with a screw-on cap having a 3.8 cm diameter hole in the center thereof and with a 4.45 cm diameter rubber washer having an approximately 3.6 cm hole in its center. The rubber washer was placed on the lip of the jar and foil/sample/foil assembly was placed backing side down on the rubber washer. The lid was then screwed loosely on the jar.

The assembly was placed in a chamber at 40 C and 20% relative humidity for four hours. At the end of four hours, the cap was tightened inside the chamber so that the sample was level with the cap (no bulging) and the rubber washer was in proper seating position.

The foil sample assembly was removed from the chamber and weighed immediately to the nearest 0.01 gram for an initial dry weight, W1. The assembly was then returned to the chamber for at least 18 hours, the exposure time T1 in hours, after which it was removed and weighed immediately to the nearest 0.01 g for a final dry weight, W2. The MVTR in grams of water vapor transmitted per square meter of sample area per 24 hours can then be calculated using the following formula.

Upright(Dry)MVTR=$(W1-W2)*(4.74*104)/T1$

Inverted MVTR

The inverted MVTR was measured using the following test procedure. After obtaining the final "dry" weight, W2, as described for the upright MVTR procedures, the assembly was returned to the chamber for at least 18 additional hours of exposure time, T2, with the jars inverted so that the tap water was in direct contact with the test sample. The sample was then removed from the chamber and weighed to the nearest 0.01 gram for a final wet weight, W3. The inverted wet MVTR in grams of water vapor transmitted per square meter of sample area per 24 hours can then be calculated using the following formula.

Inverted(Wet)MVTR=$(W2-W3)*(4.74*104)/T2$

Preparative Example 1 (PE1)

Silicone diamine (WACKER FLUID NH 130D, Mn=11496, 11.5 g), polypropylene (PP-X-10082, Mn=6418, 12.84 g), and p-xylene (30 g) were charged into a flask. The solution was refluxed for 0.5 hour in an oil bath at 130° C. Evaporation of solvent at 120° C. gave solid powder (tri-block material) according to the reaction scheme below.

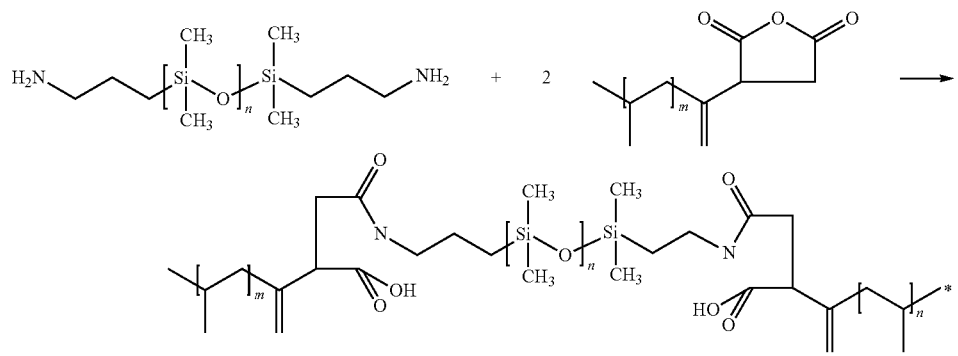

Preparative Example 2 (PE2)

Silicone diamine (WACKER FLUID NH 130D, Mn=11496, 11.5 g), polypropylene (PP-X-10082, Mn=6418, 12.84 g), p-xylene (30 g) and isoquinoline (0.04 g) were charged into a flask. The solution was refluxed for 8 hours azeotropically to take out water in an oil bath at 130° C. Evaporation of solvent at 120° C. gave solid powder (tri-block material) according to the reaction scheme below.

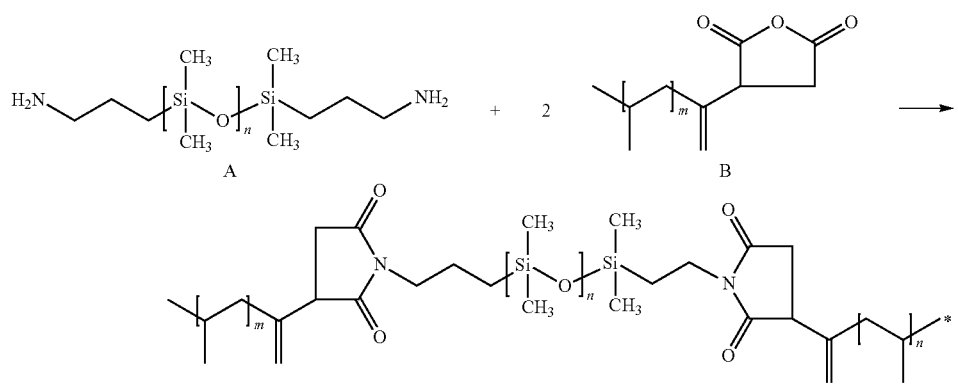

Preparative Example 3 (PE3)

Silicone diamine (WACKER FLUID NH 130D, Mn=11496, 11.5 g), polypropylene (PP-X-10053, Mn=2654, 5.3 g), and p-xylene (30 g) were charged into a flask. The solution was refluxed for 0.5 hours in an oil bath at 130° C. Evaporation of solvent at 120° C. gave solid powder (tri-block material) according to the reaction scheme below.

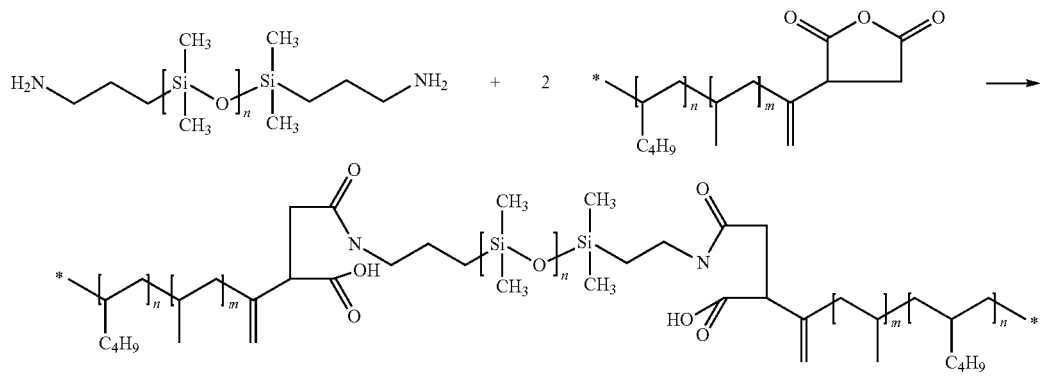

Preparative Example 4 (PE4)

Silicone diamine (WACKER FLUID NH 130D, Mn=11496, 11.5 g), polypropylene (PP-X-10053, Mn=2654, 5.3 g), p-xylene (30 g) and isoquinoline (0.04 g) were charged into a flask. The solution was refluxed for 8 hours azeotropically to take out water in an oil bath at 130° C. Evaporation of solvent at 120° C. gave solid powder (tri-block material) according to the reaction scheme below.

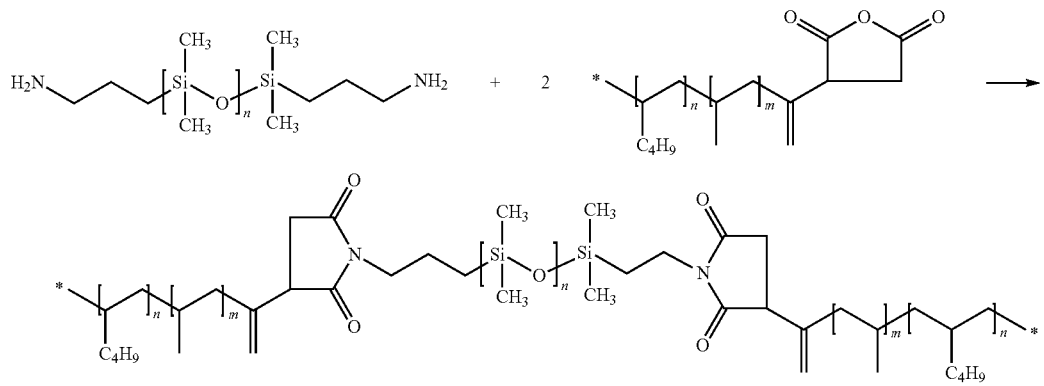

Preparative Example 5 (PE5)

Silicone diol (DMS-C21, Mn=5000, 50 g), polypropylene (PP-X-10065, Mn=1178, 23.56 g), p-xylene (80 g) were charged into a flask. The solution was refluxed for 0.5 hours in an oil bath at 130° C. Evaporation of solvent at 120° C. gave solid powder (tri-block material) according to the reaction scheme below.

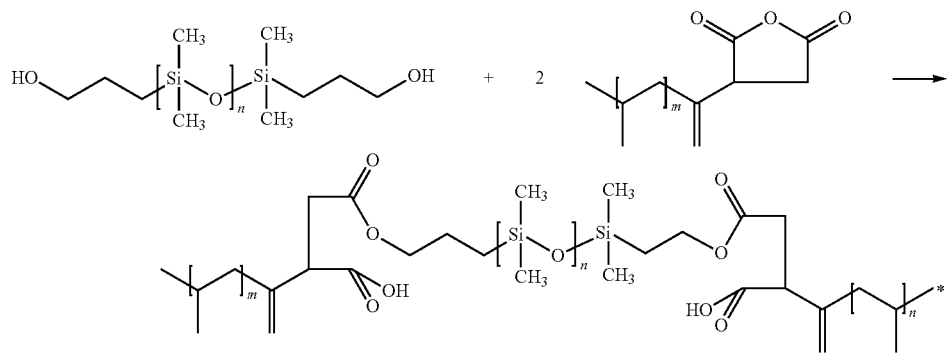

Preparative Example 6 (PE6)

Silicone monoamine (MCR-A11, Mn=900, 9 g), polypropylene (PP-X-10082, Mn=6418, 64.18 g), and p-xylene (300 g) were charged into a flask. The solution was refluxed for 0.5 hour in an oil bath at 130° C. Evaporation of solvent at 120° C. gave solid powder (di-block material) according to the reaction scheme below.

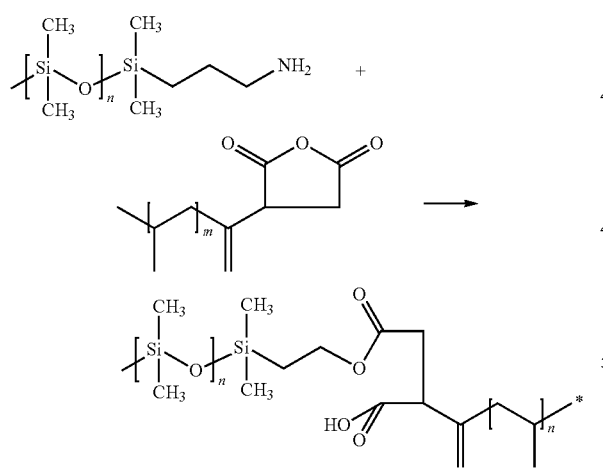

Preparative Example 7 (PE7)

Silicone monoamine (MCR-A11, Mn=900, 9 g), polypropylene (PP-X-10082, Mn=6418, 64.18 g), and p-xylene (300 g) and isoquinoline (0.04 g) were charged into a flask. The solution was refluxed for 8 hours azeotropically to take out water in an oil bath at 130° C. Evaporation of solvent at 120° C. gave solid powder (di-block material) according to the reaction scheme below.

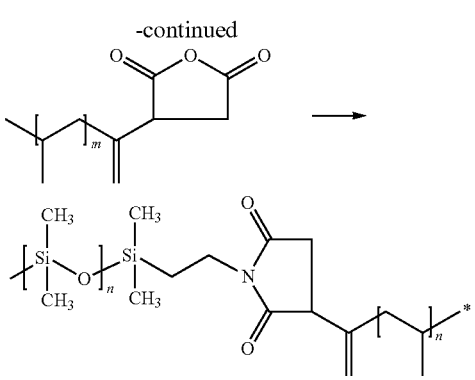

Preparative Example 8 (PE8)

Silicone multiamine (GP-4, equivalent Mn=1182.03, 11.82 g), polypropylene (PP-X-10082, Mn=6418, 64.18 g), and p-xylene (100 g) were charged into a flask. The solution was refluxed for 0.5 hour in an oil bath at 130° C. Evaporation of solvent at 120° C. gave solid powder (multi-block material) according to the reaction scheme below.

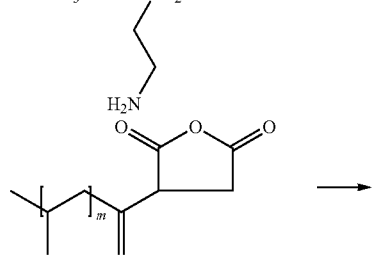

-continued

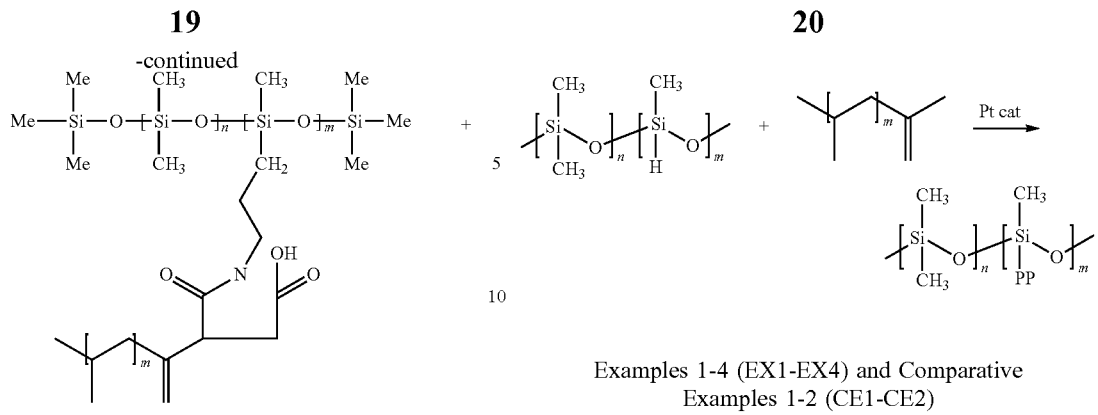

Preparative Example 9 (PE9)

Silicone multiamine (GP-4, equivalent Mn=1182.03, 11.82 g), polypropylene (PP-X-10082, Mn=6418, 64.18 g), and p-xylene (100 g) and isoquinoline (0.04 g) were charged into a flask. The solution was refluxed for 8 hours azeotropically to take out water in an oil bath at 130° C. Evaporation of solvent at 120° C. gave solid powder (multi-block material) according to the reaction scheme below, wherein m is more than 1.

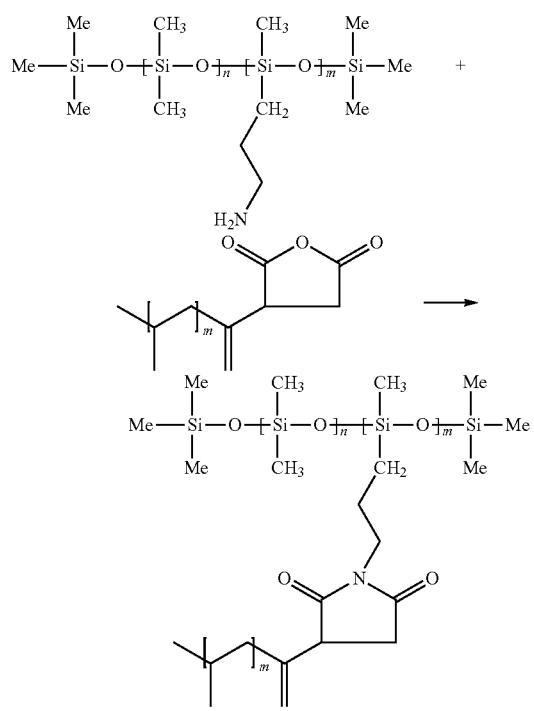

Preparative Example 10 (PE10)

Polypropylene (PP-X-10081, 3 g) and xylene (30 g) were mixed in a flask and heated until complete dissolution. The solution was cooled down and then Pt catalyst (SIP 6831.2, 0.02 g) and silicone (HMS-064 $M_n$=55K-65K, 3 g) were added. The solution was heated to 80° C. for 66 hours. Evaporation of solvent at 120° C. gave about 5.8 g of a solid powder (multi-block silicone with polypropylene side chain) according to the reaction scheme below.

Examples 1-4 (EX1-EX4) and Comparative Examples 1-2 (CE1-CE2)

First, 5 g of a tri-block polymer (prepared as described above in PE1) was dissolved in 95 g of xylene. The tri-block polymer contained 46 wt. % of silicone, and the coating solution contained 5 wt. % of the tri-block polymer. The resulting solution was then coated on ESTANE 58327 ether-based polyurethane films using a 3# Meyer bar. The resulting coated films were then dried in an oven at specified temperatures for specified time to prepare the coated films of EX1-EX4. Table 1, below summarizes the drying temperature and times used for preparing each of EX1-EX4 samples. The dried coating had a calculated thickness of about 2 microns.

CE1 was uncoated ESTANE 58327 ether based polyurethane film. CE2 was a 3M TEGADERM HP TRANSPARENT DRESSING commercially available from 3M Company, St. Paul, Minn. under trade designation "3M TEGADERM HP TRANSPARENT DRESSING".

TABLE 1

| Example | Block Copolymer | Drying temperature (° C.) | Drying time (minutes) |
| --- | --- | --- | --- |
| EX1 | PE1 | 110 | 2 |
| EX2 | PE1 | 120 | 2.5 |
| EX3 | PE1 | 130 | 2.5 |
| EX4 | PE1 | 140 | 2.5 |

EX1-EX4 and CE1-CE2 samples were then tested for their breathability (i.e., MVTR), static and kinetic coefficients of friction, and heat seal compatibility and the data are summarized in Table 2, below.

TABLE 2

| Example | K-COF | Upright MVTR (grams/m²/ 24 hours) | Inverted MVTR (grams/m²/ 24 hours) | Conditions for Heat Seal of Carrier (seconds @ ° C.) |
| --- | --- | --- | --- | --- |
| CE1 | 0.653 | 3243 | 34099 | Not tested |
| CE2 | 0.330 | Not tested | Not tested | Not tested |
| EX1 | 0.202 | 3459 | 20927 | 60 @ 132 |
| EX2 | 0.248 | 3038 | 23518 | 30 @ 132 |
| EX3 | 0.208 | 3099 | 29064 | 30 @ 132 |
| EX4 | 0.190 | 3065 | 29032 | 30 @ 135 |

What is claimed is:
1. A laminate comprising
a substrate having a major surface and opposing surface; and
a coating comprising a block copolymer disposed on major surface of the substrate wherein the block copolymer comprises a polyorganosiloxane block and a polyolefin block, the polyolefin block having a melt point of at least 110° C. wherein the block copolymer has the structure A[-L-B]$_n$ wherein n is at least 1,
A is the polyorganosiloxane block,
B is the polyolefin block comprising a polypropylene homopolymer or copolymer, and
L is a divalent linking group comprising the reaction product of an amine or hydroxyl and an anhydride; and
wherein the block copolymer comprises at least 40 wt-% of polyorganosiloxane.

2. The laminate of claim 1 wherein the coating forms an exposed surface layer.

3. The laminate of claim 2 wherein the coating provides a lower coefficient of friction than the substrate.

4. The laminate of claim 2 wherein the coating has a coefficient of friction of less than 0.30.

5. The laminate of claim 1 wherein an adhesive is disposed on the opposing surface of the substrate as the coating.

6. The laminate of claim 5 wherein the adhesive is a pressure sensitive adhesive.

7. The laminate of claim 6 wherein the laminate is wound into a roll such that the pressure sensitive adhesive contacts the coating forming a tape article.

8. The laminate of claim 6 wherein the laminate further comprises a release liner in contact with the pressure sensitive adhesive.

9. The laminate of claim 1 wherein the laminate has an upright moisture vapor transmission rate of at least 1,000 g/m$^2$/24 hours.

10. The laminate of claim 1 wherein the laminate further comprises a carrier in contact with the coating.

11. The laminate of claim 1 wherein the carrier is heat sealed through the coating to the substrate.

12. The laminate of claim 1 wherein the polyolefin block comprises a polypropylene homopolymer or copolymer.

13. The laminate of claim 12 wherein the polypropylene copolymer comprises repeat units derived from saturated alkylenes and unsaturated alkenes having 4 to 12 carbon atoms.

14. The laminate of claim 1 wherein n is 2.

15. The laminate of claim 1 wherein the block copolymer is prepared by a reaction of an amine or alcohol functional polyorganosiloxane and an anhydride terminated polyolefin polymer having a melt point of at least 110° C.

16. A medical dressing comprising the laminate of claim 1.

17. The medical dressing of claim 16 wherein a skin contact material is disposed on the opposing surface of the substrate as the coating.

18. The medical dressing of claim 17 wherein the absorbent is a hydrocolloid, polymer gel, or foam.

19. The medical dressing of claim 16 wherein the skin contact material is an adhesive, an absorbent, or a combination thereof.

20. The laminate of claim 1 wherein the polyorganosiloxane is polydimethylsiloxane.

* * * * *